United States Patent [19]

Washino et al.

[11] Patent Number: 4,905,649

[45] Date of Patent: Mar. 6, 1990

[54] FUEL PROPERTIES DETECTING APPARATUS FOR AN INTERNAL COMBUSTION ENGINE

[75] Inventors: Shoichi Washino; Satoru Ohkubo, both of Tsukaguchihonmachi, Japan

[73] Assignee: Mitsubishi Denki Kabushiki Kaisha, Tokyo, Japan

[21] Appl. No.: 250,175

[22] Filed: Sep. 28, 1988

[30] Foreign Application Priority Data

Sep. 29, 1987 [JP] Japan ................................ 62-246561

[51] Int. Cl.[4] ........................ G01N 33/22; F02D 41/04

[52] U.S. Cl. ...................................... 123/435; 73/117.3

[58] Field of Search .................... 123/425, 435; 73/35, 73/117.3

[56] References Cited

U.S. PATENT DOCUMENTS

| | | | |
|---|---|---|---|
| 4,397,285 | 8/1983 | O'Neill | 123/425 X |
| 4,466,408 | 8/1984 | Cheklich | 123/425 |
| 4,788,854 | 12/1988 | Javaherián | 73/117.3 |

FOREIGN PATENT DOCUMENTS

| | | |
|---|---|---|
| 3523230 | 1/1986 | Fed. Rep. of Germany . |
| 3527856 | 2/1986 | Fed. Rep. of Germany . |
| 3635963 | 5/1987 | Fed. Rep. of Germany . |
| 78480 | 5/1985 | Japan . |
| 60-212643 | 10/1985 | Japan . |
| 63-15466 | 4/1988 | Japan . |

*Primary Examiner*—Tony M. Argenbright

*Attorney, Agent, or Firm*—Oblon, Spivak, McClelland, Maier & Neustadt

[57] ABSTRACT

A fuel properties detecting aparatus for an internal combustion engine has a pressure detector to detect an inner pressure of cylinder, a crank angle detector to detect a crank angle of engine, and a control device which is adapted to receive signals from the pressure detector and the crank angle detector to thereby calculate an effective calorific value Q of fuel in an ignition cycle on the basis of an inner pressure of a cylinder $P(\theta)$ at a crank angle in compression and expansion strokes in an ignition cycle, a crank angle $\theta$ and a cylinder capacity $V(\theta)$, and to obtain an effective combustion rate K or a low level calorific value Hu of fuel. Fuel properties are detected by using at least one of the effective combustion rate K and the low level calorific value Hu, or a ratio of a fuel injection pulse width Ti to the low level calorific value Hu (Ti/Hu).

6 Claims, 5 Drawing Sheets

| BASIC INJECTION QUANTITY Tp (ms) \ ENGINE REVOLUTION SPEED (rpm) | 800 | 2000 | 3200 | 4000 | 4800 | 5600 | 6400 |
|---|---|---|---|---|---|---|---|
| | 20 | 30 | 30 | 40 | 40 | 40 | 40 |
| 5 | 15 | 20 | 20 | 20 | 30 | 30 | 40 |
| 4 | 10 | 10 | 10 | 15 | 20 | 25 | 35 |
| 3 | 10 | 0 | 0 | 10 | 15 | 20 | 30 |
| 2 | 10 | 0 | 0 | 10 | 15 | 20 | 25 |
| 1 | 10 | 0 | 0 | 10 | 15 | 20 | 20 |
| 0 | | | | | | | |

FUEL PROPERTIES DETECTING APPARATUS FOR AN INTERNAL COMBUSTION ENGINE

BACKGROUND OF THE INVENTION

1. Field of the Invention

The present invention relates to a fuel properties detecting apparatus for an internal combustion engine to detect the properties of fuel such as alcohol mixed with gasoline to be supplied to the internal combustion engine.

2. Discussion of Background

Various types of apparatus for detecting the properties of fuel have been known. Most such apparatuses are of a type which uses an alcohol sensor. There are few conventional apparatuses or methods without using the alcohol sensor.

As an example of a method of detecting the properties of fuel, description concerning Japanese Unexamined Patent Publication 78480/1985, which discloses a technique close to the present invention although it concerns a technique of ignition timing control, will be made.

FIG. 7 is a block diagram of a fuel properties detecting apparatus used for a conventional fuel properties detecting method, and FIG. 8 is a diagram showing major parts of the apparatus used for the conventional fuel properties detecting method.

In FIG. 8, a reference numeral 5 designates a cylinder block of engine, numeral 22 designates a knocking sensor attached to the block 5, a numeral 11 designates an ignition plug, a numeral 24 designates a distributer, a numeral 25 designates a crank angle sensor, a numeral 25 designates a control device, a numeral 4 designates an intake manifold, a numeral 12 designates an air-flow sensor, a nemeral 23 designates an igniter and a numeral 10 designates a fuel injection valve.

A basic operation in the conventional apparatus will be described.

As shown in a block diagram in FIG. 7, a knocking sensor A detects vibrations of pressure in an engine caused during combustion. A knocking level discriminating means B discriminates presence or absence of a knocking on the basis of a signal generated from the knocking sensor A. A lag angle control means C controls a lag angle in ignition timing when a knocking occurs. A lead angle control means D controls to advance the ignition timing when there occurs no knocking. A property change detecting means F detects change in a knocking generation level corresponding to an advanced angle in ignition timing. A maximum lag angle limit operating means G operates the maximum limit value of a lag angle provided from the lag angle control means C on the basis of change in properties detected by the property change detecting means F. The above-mentioned means constitute an ignition timing control apparatus.

The operation of the ignition timing control apparatus will be described.

The ignition timing control apparatus is operated in such a manner that when the property change detecting means F detects a change in properties of knocking generation level corresponding to an amount of lead angle in ignition timing, determination of the properties of fuel, for instance, whether gasoline used for the engine is regular gasoline for a high octane gasoline, is made. Then, the maximum lag angle limit operating means G determines the maximum limit value of lag angle by the lag angle control means C, whereby the optimum value is operated. When the knocking level discriminating means B judges that there is a knocking, the knocking level is maintained by causing an angle of ignition timing to be lagged to the maximum limit value. FIG. 9 shows change in properties of a knocking generating level corresponding to an amount of lead angle in ignition timing, which changes depending on a kind of gasoline, such as regular gasoline or a high octane gasoline.

In FIG. 9, a broken line indicates a relation of a torque to a knocking level when the regular gasoline is used and solid line shows a relation of them when the high octane gasoline is used.

Now, assuming that regular gasoline is used. When a predetermined basic ignition timing is at a point B, the knocking level corresponding to the point D becomes a trace level. However, when a high octane gasoline is used while the basic ignition timing is kept unchanged, there takes place no knocking at all, and when the ignition timing is advanced to a point C, the knocking level becomes the trace level. In other words, there can be found the properties of fuel of either regular gasoline or a high octane gasoline by detecting the change of knocking generation level with respect to the lead angle quantity of ignition timing.

Generally, it is well-known that an octane value is changed by mixing alcohol in gasoline. In consideration of the above-mentioned fact and the change of knocking generation level with respect to the lead angle quantity, presence or absence of alcohol in gasoline can be detected by the knocking sensor 22 for detecting a knocking level change. Namely, when the output of the knocking sensor 22 is supplied to a filter having a knocking frequency as a cut-off frequency or the frequencies of higher harmonics in order to examine the magnitude of the output with respect to the lead angle quantity in ignition timing, the magnitude of the output is small when some amount of alcohol is mixed with gasoline and the same ignition timing is used. Accordingly, by previously determining the ignition timing in a level such as K1 or K2, absence or presence of alcohol in gasoline can be detected by a knocking level change.

In the conventional fuel properties detecting apparatus having the above-mentioned construction, it was impossible to detect the properties of fuel unless a knocking takes place. Further, it was impossible to detect quantitatively the content of alcohol in gasoline.

SUMMARY OF THE INVENTION

It is an object of the present invention to provide a fuel properties detecting apparatus capable of detecting quantitatively the content of alcohol mixed with gasoline regardless of a knocking occuring.

The foregoing and the other objects of the present invention have been attained by providing a fuel properties detecting apparatus for an internal combustion engine wherein an intake air quantity, and an air-fuel ratio in exhaust gas are measured, a basic fuel injection quantity is calculated on the basis of the intake air quantity and an amount of fuel to be injected is feed-back controlled in response to the air-fuel ratio, characterized by comprising:

a pressure detecting means to detect an inner pressure of a cylinder, a crank angle detecting means to detect a crank angle of the engine, and a control device adapted to receive signals from the pressure detecting means and the crank angle detecting means to thereby calculate an effective calorific value Q of fuel in an ignition cycle on the basis of a inner pressure of cylinder $P(\theta)$ at a crank angle in compression and expansion strokes in an ignition cycle, a crank angle $\theta$ and a cylinder capacity $V(\theta)$, and to obtain an effective combustion rate K or a low level calorific value Hu of fuel, whereby fuel properties are detected by using at least one of the effective combustion rate K and the low level calorific value Hu, or a ratio of a fuel injection pulse width Ti to the low level calorific value Hu (Ti/Hu).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF PREFERRED EMBODIMENTS

Figure 1:
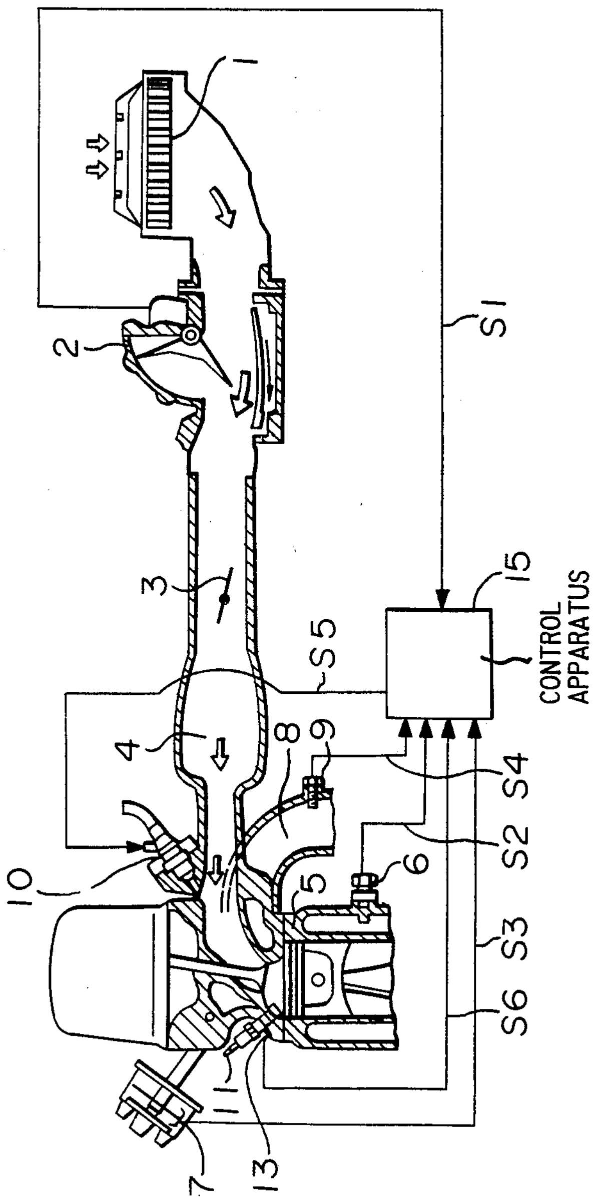
FIG. 1 is a diagram showing an embodiment of the fuel properties detecting apparatus for an internal combustion engine according to the present invention.

Referring to the drawings, wherein the same reference numerals designate the same or corresponding parts throughout the several views, and more particularly to FIG. 1, there is shown a diagram of an embodiment of the fuel properties detecting apparatus of the present invention.

In FIG. 1, a reference numeral 1 designates an air cleaner, a numeral 2 designates an air-flow meter to detect an amount of air to be sucked, a numeral 3 designates a throttle valve, a numeral 5 designates a cylinder block, a numeral 6 designates a water temperature sensor to detect the temperature of cooling water for the engine, a numeral 7 designates a crank angle sensor, a numeral 8 designates an exhaust manifold, a numeral 9 designates an exhaust gas sensor to detect a concentration of an exhaust gas component (such as a concentration of oxygen), a numeral 10 designates a fuel injection valve, a numeral 11 designates an ignition plug, a numeral 13 designates a pressure sensor to detect an inner pressure of the cylinder, a numeral 15 designates a control device.

The crank angle sensor 7 is adapted to output a reference position pulse at every reference position of the crank angle (for instance, every 180° in a four cylinder engine and every 120° in six cylinder engine) and to output a unit angle pulse at every unit angle (for instance, every 1°). The control device 15 counts the number of the unit angle pulses upon receiving a reference position pulse to thereby obtain the crank angle after the receiving of the reference position pulse. Further, in the control device 15, a revolution speed of the engine is obtainable by measuring the frequency or the period of the unit angle pulses.

In the apparatus shown in FIG. 1, the crank angle sensor 7 is installed in a distributor.

Figure 2:
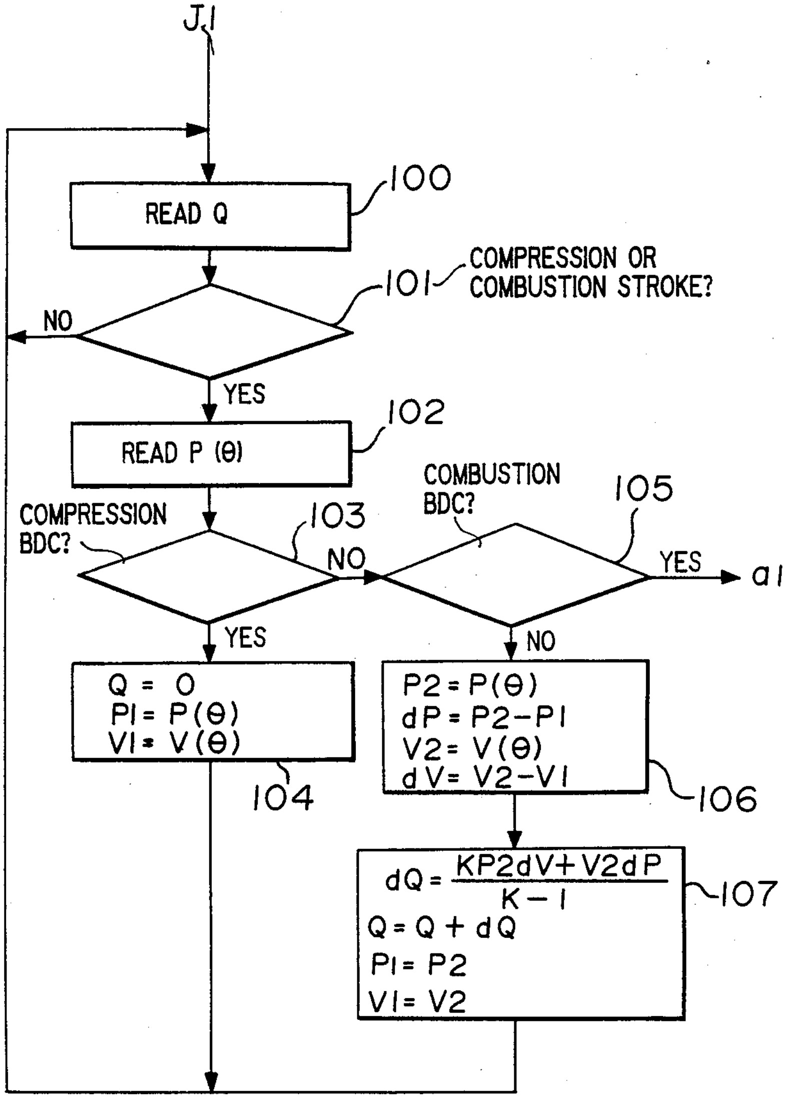
FIG. 2 is a flow chart for calculation of an effective calorific value Q according to the embodiment shown in FIG. 1.

In the control device 15 in accordance with this embodiment of the present invention, information processing to obtain an effective calorific valve Q which is used for detecting an alcohol content as shown in FIG. 2 is effected in addition to the ordinary processing of a fuel control. Description of the fuel control will first be made.

The control device 15 is constituted by a microcomputer consisting, for instance, of a CPU, a RAM, a ROM, and an input/output interface and so on.

The control device 15 receives a signal of intake air quantity S1 from the air-flow meter 2, a crank angle signal S3 from the crank angle sensor 7, a signal of exhaust gas S4 from the exhaust gas sensor 9, and a signal of water temperature S2 from the water temperature sensor 6. The control device 15 also receives a signal of battery voltage and a signal indicative of the throttle valve being fully closed, although the signals are not shown in FIG. 1. The control device operates the input signals to calculate a fuel injection quantity to be supplied to the engine, whereby a fuel injection signal S5 is generated. The signal S5 actuates a fuel injection valve 10 to thereby feed a predetermined amount of fuel to the engine.

Figures 3, 4:
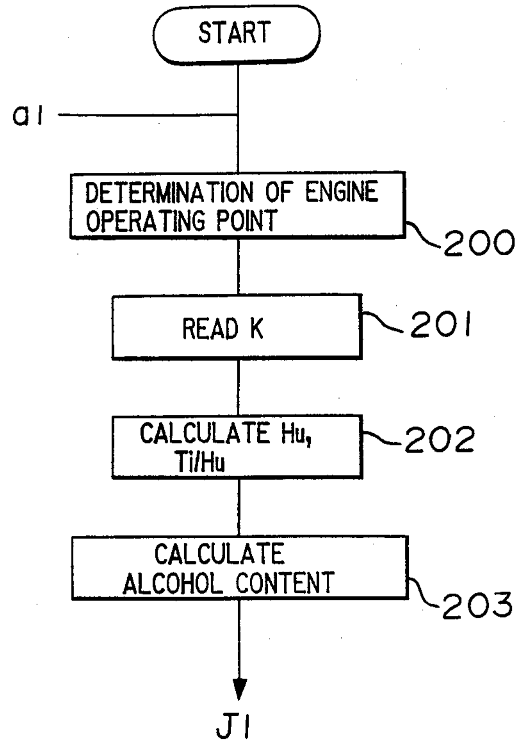
FIG. 3 is a flow chart to obtain alcohol content for the above-mentioned embodiment.
FIG. 4 is a diagram showing collection coefficients under conditions of heavy load for the above-mentioned embodiment.

Operations to obtain an fuel injection quantity Ti are carried out in the control device 15 by using the following equation:

$$Ti = Tp \times (1 + Ft + KMR/100) \times \beta + Ts \quad (1)$$

where Tp is a basis injection quantity which is obtained by $Tp = K_0 \times A/F \times Ga/N$ wherein Ga is an intake air quantity, N is an engine revolution speed, A/F is an air-fuel ratio, $K_0$ is a constant, Ft is a correction coefficient corresponding to the temperature of cooling water for the engine, which assumes a large value when the temperature of cooling water is low, KMR is a complementary coefficient at a heavy load, which can be taken from a data table which is previously prepared including values corresponding to the basic injection quantity Tp and the revolution speed N as shown in FIG. 4, Ts is a correction coefficient depending on a battery voltage, which is a coeffieient for correcting variations in voltage which actuates the fuel injection valve 10, and $\beta$ is a correction coefficient corresponding to the signal of exhaust gas S4 of the exhaust gas sensor 9. By using the coefficient $\beta$, it is possible to effect a feed-back control of air-fuel ratio of a gas mixture for a predetermined value such as a value of a theoretical air-fuel ratio of 14.6.

In this case, when the feed-back control is effected by using the exhaust gas signal S4, correction by the coefficients Ft and KMR becomes meaningless since the air-fuel ratio of the gas mixture is controlled so that it has always a constant value. Accordingly, the feed-back control by the exhaust gas signal S4 is carried out only when the correction coefficients Ft and KMR are zero.

Description will be made as to data processings to obtain the effective calorific value Q for detecting an alcohol content which is essential to the present invention with reference to FIG. 2. First of all, the principle of detecting an alcohol content will be described. The following formula is established from the first law of thermodynamics:

$$dQ=du+Pdv$$

By substituting the following formulas du=cvdT (specific internal energy), Pv=RT (an equation of state) and dT=(Pdv+vdP)/R in the right item in the above-mentioned equation, the following equation (1) is obtainable:

$$dQ = \frac{1}{k-1}\{KPdv + vdP\} \quad (1)$$

where K is a ratio of specific heat. When integrating the equation (1), the following equation (2) can be obtained:

$$Q = \frac{1}{k-1}[K \int P(\theta)dV(\theta) + \int V(\theta)dP(\theta)] \quad (2)$$

Namely, a net calorie (effective calorific value) Q given to a working gas in an ignition cycle is given by the equation (2), and it is obtained by integrating the equation (1) if an inner pressure of the cylinder at each crank angle $P(\theta)$ and a cylinder capacity at the crank angle $V(\theta)$ are known.

On the other hand, since the net calorie (effective calorific value) Q given to the working gas in an ignition cycle is obtained by the difference between a calorie Qr produced in combustion and a calorie Qd released from the cylinder wall, the following equation (3) is obtained:

$$Q=Qr-Qd \quad (3)$$

When the weight of air sucked in an ignition cycle (air flow rate/revolution speed), a fuel-air ratio and a low level calorific value of fuel are respectively represented by Ga, F/A and Hu, a relation of Qr=Hu×(F/A)×Ga is established. When the heat loss Qd is represented in terms of (Kd×Hu×(F/A)×Ga), the following equation (4) is obtainable:

$$Q=(1-Kd)Hu\times(F/A)\times Ga=K\times Hu\times(F/A)\times Ga \quad (4)$$

In the equation (4), K is an index indicating how much heat was effectively used with respect to heat produced by combustion, namely it is a parameter representing an effective combustion rate. Kd represents a rate of heat loss in heat produced by combustion. Kd (hence, K) can be considered to be a parameter which does not substantially change even though fuel is changed.

It is because the calorific value Hs of a theoretical gas mixture per unit volume does not substantially change even though fuel is changed as shown in Table I, and accordingly, a combustion temperature does not change, hence, a heat loss does not show a substantial change. In this case, there is a possibility that K is changed depending on an ignition timing and an engine operating temperature (for instance, a cooling water temperature and a cylinder wall temperature). This is because the parameter K may be changed by the change of heat loss due to the change of ignition timing and engine operating temperature even when the same engine is used since the parameter K is a parameter corresponding to a graphically represented fuel consumption rate. Generally, an ignition timing has to be previously determined so as to correspond to an operating point of engine, and basically, it is not changed even though fuel is changed. When an engine operating temperature is changed, the parameter K is changed depending on the engine operating temperature. However, the value of parameter K is primarily determined by giving an engine operating point and an operating temperature. Accordingly, when an engine to be used is specified, it is possible to previously obtain a value of K which corresponds to the engine operating point and the engine operating temperature, the value K being able to be stored in a data table. In preparing the data table, any one in combination of "a torque and an engine revolution number" or "an intake air pipe pressure and an engine revolution number" or "an intake air flow rate per unit revolution number may be provided and an engine revolution number".

As the engine operating temperature, a cooling water temperature or a cylinder wall temperature may be used. From this, when the parameter K is obtained with respect to an engine to be used, a ratio A/F is obtained from a signal from the exhaust gas sensor, and a value Ga is obtained from the signals of the air-flow meter and the engine revolution number. Accordingly, a low level calorific value Hu of fuel can be calculated on the basis of the above-mentioned value Q (by using the equation (3)).

As shown in FIG. 4, it is possible to estimate from the low level calorific value Hu that what fuel is used for the engine. For instance, since the low level calorific value Hu of methanol is about half that of gasoline, it can sufficiently be estimated from the low level calorific value Hu what fuel is used and how much is the content.

Figure 5:
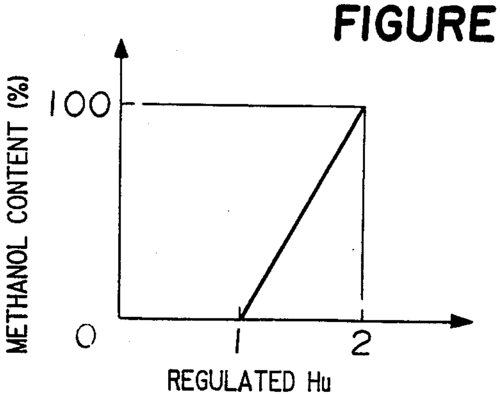
FIG. 5 is a characteristic diagram showing the relation between an alcohol content and a regulated low level calorific value Hu.

FIG. 5 shows the relation between a methanol content and a regulated low level calorific value Hu wherein the abscissa represents a regulated low level calorific value Hu, and the ordinate represents a methanol content. As seen from FIG. 5, the methanol content is 0% when a regulated low level calorific value Hu is 1, and 100% when the value Hu is 2. Accordingly, the relation between the methanol content and the regulated low level calorific value Hu can be given as a linear line which connects these two points.

TABLE 1

| Fuel | Specific gravity (15° C.) | Low level calorific value (Hu) kcal/kg | Low level calorific value (Hu) kcal/l | Heat of vaporization (kcal/kg) | Theoretical mixing ratio | Volume increase by combustion | Calorific value Hs of theoretical gas mixture |
|---|---|---|---|---|---|---|---|
| Gasoline (D) | 0.758 | 10430 | 7900 | 73 | 14.6 | 1.047 | 913.5 |
| Pentane | 0.629 | 10890 | 6850 | 83 | 15.25 | 1.051 | 961.6 |

TABLE 1-continued

| Fuel | Specific gravity (15° C.) | Low level calorific value (Hu) kcal/kg | kcal/l | Heat of vaporization (kcal/kg) | Theoretical mixing ratio | Volume increase by combustion | Calorific value Hs of theoretical gas mixture |
|---|---|---|---|---|---|---|---|
| Hexane (80%) | 0.683 | 10690 | 7300 | 86 | 15.2 | 1.051 | 910.6 |
| Heptane (97%) | 0.689 | 10700 | 7370 | 75 | 15.1 | 1.056 | 911.9 |
| Octane (pure) | 0.718 | 10670 | 7660 | 71 | 15.05 | 1.058 | 903.9 |
| Benzole (pure) | 0.882 | 9640 | 8500 | 95 | 13.2 | 1.013 | 935.9 |
| Toluol (99%) | 0.868 | 9730 | 8440 | 84 | 13.4 | 1.023 | 927.9 |
| Xylol (91%) | 0.860 | 9890 | 8500 | 81 | 13.6 | 1.03 | 923.1 |
| Cyclohexane (93%) | 0.784 | 10400 | 8190 | 86 | 14.7 | 1.044 | 913.5 |
| Ethyl alcohol (pure) | 0.790 | 6540 | 5170 | 220 | 8.97 | 1.065 | 907.1 |
| Ethyl alcohol (95%) | 0.812 | 6040 | 4900 | 246 | 8.4 | 1.065 | 873.5 |
| Methanol (pure) | 0.79 | 4880 | 3855 | | 5.0 | | |

Figure 6:
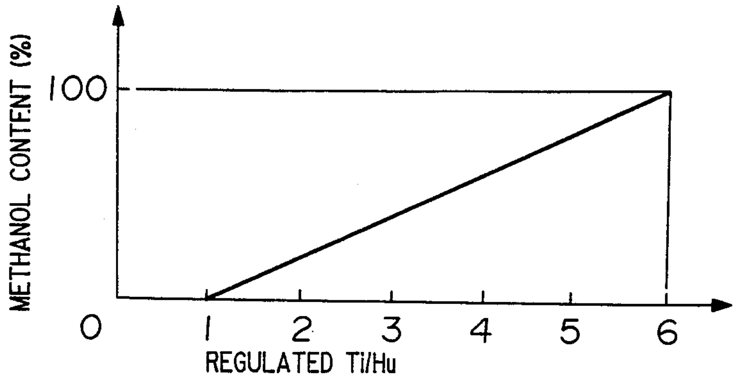
FIG. 6 is a characteristic diagram showing the relation between an alcohol content and a regulated ratio of Ti/Hu.
Figure 7:
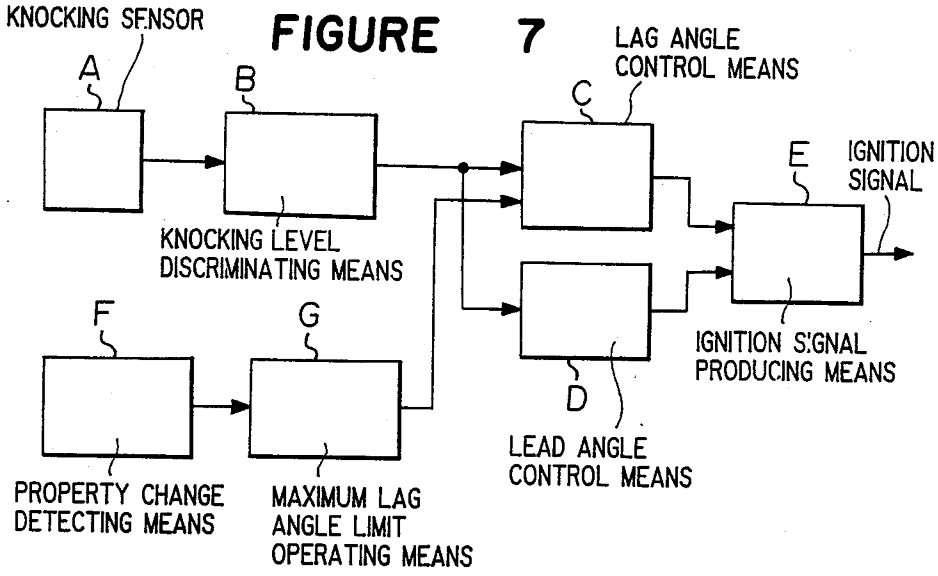
FIG. 7 is a block diagram of a conventional fuel properties detecting apparatus.
Figure 8:
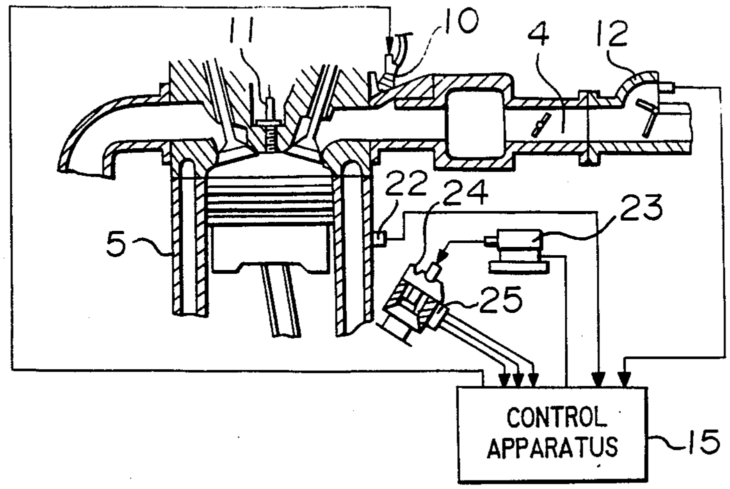
FIG. 8 is a diagram showing a conventional fuel control apparatus applied for a conventional fuel properties detecting method.
Figure 9:
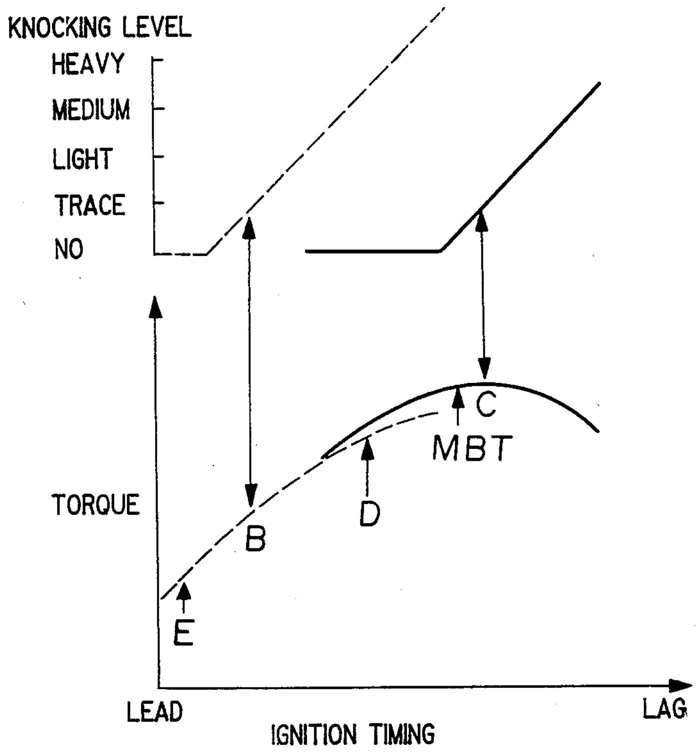
FIG. 9 is a characteristic diagram of knocking generation level to illustrate a conventional fuel properties detecting method.

Accordingly, it is possible to obtain quantatatively the methanol content from the data of regulated low level calorific value Hu. In order to obtain further accurate value, it is desirable to calculate a value Ti/Hu. When methanol is used, its theoretical air-fuel ratio is "5". Accordingly, Ti is 2.92 times as much as gasoline, i.e., 14.6/5. In comparing of a value Ti/Hu, there is about 6 times. Namely, as shown in FIG. 6, the relation between the methanol content and the regulated value of Ti/Hu is given by a linear line connecting to points (1, 0%) and (1, 100%). Accordingly, it is possible to increase accuracy three times as large as the case where the methanol content is obtained only from the regulated low level calorific value Hu. Description will be made by using FIG. 2 in which a sampling crank angle of each 1° is used.

At step 100, a crank angle $\theta$ is read. At Step 101, determination is made as to whether or not the crank angle read is in compression and expansion (combustion) strokes. When "YES", an inner pressure of cylinder $P(\theta)$ at the instant time is read (Step 102). On the other hand, when "NO", the Step 100 is again taken to wait for the next crank angle.

At step 103, determination is made as to whether or not the crank angle $\theta$ read at Step 100 is in a compression BDC. When "YES", then, an initiallization step is taken. Namely, at Step 104, values Q, P1 and V1 are respectively set to 0, $P(\theta)$ and $V(\theta)$ and the sequential step is returned to Step 101. When "NO" at Step 103, Step 105 is taken at which determination is made as to whether or not the crank angle read at Step 100 is in a combustion (expansion) BDC. When "NO", a value dQ is calculated at Steps 106, 107 and then, the sequential Step is returned to Step 100.

On the other hand, when, "YES" at Step 105, a routine as shown in FIG. 3 is executed. Namely, at Step 200, an engine operating point is determined. At Step 201, a value K corresponding to the engine operating point is read and at Step 202, a low level calorific value Hu and a value Ti/Hu are obtained.

Calculations as shown in FIG. 2 have to be carried out at an extremely high speed to such extent that the entire part of the routine of FIG. 2 is finished in a time of crank angle of 1°. Such high speed calculation is possible by using, for instance, a data-drive type processor (such as μPD7281, manufactured by Nippon Denki Kabushiki Kaisha) as a coprocessor. Namely, a host processor (which may be an ordinary Neumann processor) is used for carrying out calculations in the main routine and it is sufficient to use a coprocessor (a data-drive type processor) for carrying out calculations as shown in FIG. 2. In the main routine by the host processor, operations of fuel control (such as the calculation of the pulse width Ti of a fuel injection signal and judgement of an engine operating point), a control of a flow of operations of the routine in FIG. 2 and the operations as shown in FIG. 3 are conducted.

With this respect, a detailed explanation will be made. Namely, since the data-drive type processor is so adapted that operations are carried out in accordance with data, the flow of operations for carrying out the routine as in FIG. 2 is controlled by utilizing the feature of the processor as follows.

For instance, when a crank angle signal is input to the host processor, the host processor supplies the data of crank angle and inner pressure of cylinder ($P\theta$) to the coprocessor which stores the operating program as in FIG. 2. This is because the data-drive type processor automatically operates as long as necessary data are provided. And, it is sufficient that the data-drive type processor returns the data of Q as a result of integrating operations when the content of Step 105 in the operating program as in FIG. 2 is satisfied. Then, it is sufficient that the host processor which receives the data carries out the routine as in FIG. 3 so that the value K corresponding to the engine operating point is read; the low level calorific value Hu and Ti/Hi (or these regulated values) are calculated, and the alcohol content is determined with reference to FIGS. 5 and 6 (Step 203).

When a self-supporting type processor is used for the data-drive type processor, it is unnecessary to use the host processor and the coprocessor separately, and it is sufficient to use the data-drive type processor as a host processor to carry out all operations.

Since the cylinder capacity $V(\theta)$ and the differential value $dV(\theta)$ in the routine as in FIG. 2 are known values, they can previously be memorized in a one-dimensional data table concerning $\theta$, and can be used by the data-drive type processor. In this case, a time for operation can be shortened.

Thus, in accordance with the present invention, a calorific value Q in an ignition cycle is obtained on the basis of an inner pressure of cylinder $P(\theta)$ and a cylinder capacity $V(\theta)$ and a low level calorific value Hu of fuel and Ti/Hu are calculated to thereby obtained quantatively an alcohol content without causing a knocking.

Obviously, numerous modifications and variations of the present invention are possible in light of the above teachings. It is therefore to be understood that within the scope of the appended claims, the invention may be practiced otherwise than as specifically described herein.

What is claimed is:

1. A fuel properties detecting apparatus for an internal combustion engine wherein an intake air quantity and an air-fuel ratio in exhaust gas are measured, a basic fuel injection quantity is calculated on the basis of said intake air quantity, and an amount of fuel to be injected is feed-back controlled in response to said air-fuel ratio, comprising:

a pressure detecting means to detect an inner pressure of a cylinder, a crank angle detecting means to detect a crank angle of the engine, and a control device comprising means for receiving signals from said pressure detecting means and said crank angle detecting means to thereby calculate an effective calorific value Q of fuel in an ignition cycle on the basis of an inner pressure of a cylinder $P(\theta)$ at a crank angle in compression and expansion strokes in an ignition cycle, a crank angle $\theta$ and a cylinder capacity $V(\theta)$, and to obtain an effective combustion rate K or a low level calorific value Hu of fuel, whereby said control device further comprises means for detecting fuel properties by using at least one of said effective combustion rate K said low level calorific value, Hu, and a ratio of a fuel injection pulse width Ti to said low level calorific value Hu (Ti/Hu).

2. The fuel properties detecting apparatus according to claim 1, including means for obtaining at least one of said effective combustion rate K and said low level calorific value Hu of fuel from a two-dimensional data table in which two parameters are used to indicate an engine operating point.

3. The fuel properties detecting appartus according to claim 2, wherein said two parameters indicating the engine operating point are one pair from the group of pairs of parameters consisting of a torque and an engine revolution number, an intake air pipe pressure and an engine revolution number, and an intake air quantity per unit revolution number and an engine revolution number.

4. The fuel properties detecting apparatus according to claim 2, wherein said two-dimensional data table is prepared with each parameter indicating a temperature condition of engine.

5. The fuel properties detecting apparatus according to claim 4, wherein said each parameter indicating the temperature condition of engine is at least one of a temperature of cooling water for engine and a temperature of cylinder wall.

6. The fuel properties detecting apparatus according to claim 1, wherein said control device comprises means for calculating said calorific value Q in an ignition cycle by using an equation:

$$Q = \frac{1}{k-1}\left[K \int P(\theta)dV(\theta) + \int V(\theta)dP(\theta)\right]$$

where K is a ratio of specific heat, and means for reading a value of cylinder capacity $V(\theta)$ at a crank angle $\theta$ and a value of change $dV(\theta)$ at each crank angle $V(\theta)$ which are memorized as a data table in memories.

* * * * *